United States Patent
Bollé

[11] Patent Number: 5,956,115
[45] Date of Patent: Sep. 21, 1999

[54] SPORT GLASSES

[75] Inventor: Maurice Bollé, Oyonnax, France

[73] Assignee: Etablissements Bolle' S.N.C., Oyonnax, France

[21] Appl. No.: 08/969,720

[22] Filed: Nov. 13, 1997

Related U.S. Application Data

[63] Continuation-in-part of application No. 29/077,455, Oct. 6, 1997, abandoned.

[51] Int. Cl.$^6$ .................................................. G02C 11/08
[52] U.S. Cl. ............................... 351/62; 351/41; 351/44; 2/436
[58] Field of Search .................... 351/41, 44, 62, 351/103, 105, 106, 108, 109, 124, 131, 133, 123; 2/436

[56] References Cited

U.S. PATENT DOCUMENTS

| | | | |
|---|---|---|---|
| D. 152,502 | 1/1949 | Stegeman | D16/314 |
| D. 204,417 | 4/1966 | Shindler | D16/326 |
| D. 322,975 | 1/1992 | Bollé | D16/314 |
| D. 323,333 | 1/1992 | Jannard et al. | D16/314 |
| D. 324,528 | 3/1992 | Jannard | D16/102 |
| D. 325,040 | 3/1992 | Jannard | D16/102 |
| D. 328,468 | 8/1992 | Jannard | D16/101 |
| D. 329,442 | 9/1992 | Jannard | D16/102 |
| D. 330,035 | 10/1992 | Jannard | D16/102 |
| D. 330,903 | 11/1992 | Jannard | D16/116 |
| D. 347,017 | 5/1994 | Bollé | D16/112 |
| D. 362,011 | 9/1995 | Kolentsi | D16/315 |
| D. 379,633 | 6/1997 | Garneau | D16/315 |
| D. 381,674 | 7/1997 | Bernheiser | D16/326 |
| D. 384,364 | 9/1997 | Yee | D16/330 |
| D. 388,453 | 12/1997 | Lin | D16/315 |
| 4,515,448 | 5/1985 | Tackles | 351/41 |
| 4,730,915 | 3/1988 | Jannard | 351/47 |
| 5,054,903 | 10/1991 | Jannard et al. | 351/123 |
| 5,208,614 | 5/1993 | Jannard | 351/41 |
| 5,359,370 | 10/1994 | Mugnier | 351/41 |
| 5,387,949 | 2/1995 | Tackles | 351/121 |
| 5,412,438 | 5/1995 | Bollé | 351/44 |
| 5,576,775 | 11/1996 | Bolle | 351/62 |

FOREIGN PATENT DOCUMENTS 2.049.430  3/1971  France .

Primary Examiner—Huy Mai
Attorney, Agent, or Firm—Holland & Hart LLP

[57] ABSTRACT

Sport glasses are disclosed which include a frame having a substantially laterally extending arcuate upper portion, a nose piece integral with and centrally depending therefrom, and a pair of temples, which are hingedly mounted to the frame. A pair of convex lenses are mounted in the frame, each lens having an exposed side edge having a concave portion and an exposed lower edge having a concave portion. When the glasses are worn, the exposed edges of the lenses substantially conform to but are spaced apart from the adjacent facial structure of the wearer. In a preferred embodiment, the lenses are detachable and replaceable by the wearer. In another preferred embodiment, a pair of slots are formed in the upper portion of the frame, providing ventilation and minimizing fogging of the lenses when the sports glasses are worn by the wearer. In yet another preferred embodiment, gripping members are mounted to the rearward portion of the temples, with the gripping members terminating at the temple ends and flush with the surface of the temples at a point intermediate the temple ends and the hinged portion of the temples.

11 Claims, 4 Drawing Sheets

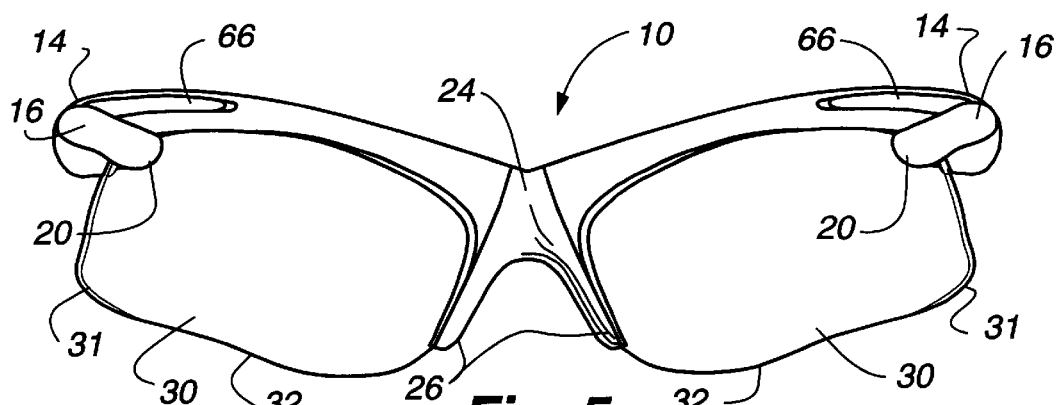
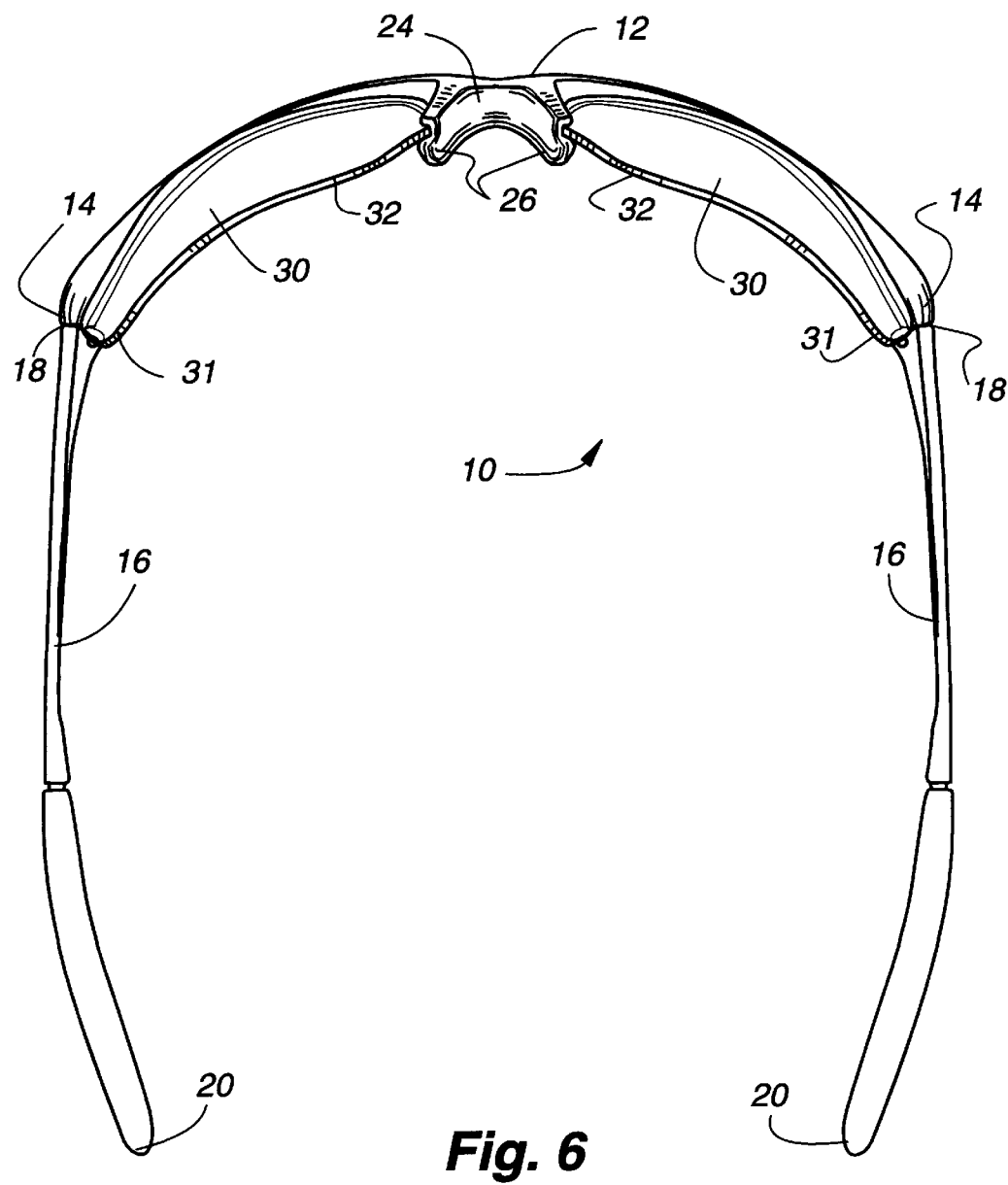

SPORT GLASSES

This application is a CIP of application Ser. No. 29/077,455 filed Oct. 6, 1997, now abandoned.

FIELD OF THE INVENTION

The present invention relates to eyeglasses such as sunglasses. More particularly, the present invention relates to eyeglasses for use outdoors, and are especially suitable for use by spectators or participants in outdoors sports.

BACKGROUND OF THE INVENTION

Sport glasses having a unitary wraparound lens are known. More particularly, a single arcuately molded lens for use during outdoor activities having a pair of opposing downwardly facing concavities formed in the bottom edge is known. Such lens configurations are commonly designed to closely conform to the front and sides of a wearer's face.

Unitary lens have some drawbacks, however. For example, fogging continues to be a problem with certain unitary lens designed to conform to a wearer's face. Also, unitary lens do not commonly allow for a custom lens prescription in which the eyesight of one eye requires correction different from the correction for the other eye. Excessive flex and vulnerability to damage resulting from impact by an external object striking the centrally facing leading portion of a unitary wraparound lens remains problematical. Then, when one portion of the unitary lens is scratched or otherwise damaged, the whole lens must be replaced. Thus, there remains a need for further improvements to face-conforming sports glasses.

It is against this background that the significant improvements and advancements of the present invention have taken place.

SUMMARY OF THE INVENTION

In accordance with its major aspects, sport glasses are disclosed which include a substantially laterally extending arcuate frame, a nose piece integral with and centrally depending from the frame, and a pair of temples hingedly mounted to the frame. A pair of convex lenses are mounted in the frame, each lens having an exposed side edge with a concave, arcuate portion, and an exposed lower edge with a concave, arcuate portion.

When the sport glasses of the present invention are worn, the exposed edges of the lenses substantially conform to but are spaced apart from the adjacent facial structure of the wearer. Preferably, the lenses are detachable and replaceable by the wearer. In the preferred embodiment, a pair of horizontal ventilating slots are formed in the frame, providing ventilation and minimizing fogging of the lenses when the sports glasses are worn. The preferable configuration also includes form fitting gripping members, which enclose the rearward portion of the temples, are closed at the temple ends and flush with the surface of the temples at a point intermediate the temple ends and the hinged end of the temples.

The sport glasses of the present invention are generally conforming to the upper facial structure of the wearer, thereby providing the aerodynamic shape and open peripheral vision preferred during outdoor activities. Despite the closely confirming shape of the sport glass lenses of the present invention, fogging is decreased by limiting the extension of the lens around the side of the head of the wearer and by the ventilating slots in the frames. Ventilation provided by the ventilating slots also serves to cool the wearer.

The pair of form fitting gripping members mounted to the temple ends of the sports glasses of the present invention are shaped so as to keep the glasses in place during athletic activity, without the uncomfortable bulkiness associated with after market tubular gripping members mounted to separately purchased sun glasses. In particular, the slim leading edges of the gripping members, which are flush at the point of intersection with the mid portion of the temple, together with the narrowed tip, minimize irritation to the back of the ear and side of the head of the wearer.

The removable configuration of lens pairs of the present invention allows for ready substitution of lenses having different tinting or prescription. Indeed, a lens pair of the present invention may have different prescriptions thus allowing for differential correction of the vision both eyes.

A more complete appreciation of the present invention and its scope can be obtained from the following description of the drawings, detailed description of presently preferred embodiments of the invention, and the appended claims.

DESCRIPTION OF THE DRAWING

FIG. 5 is a rear elevation view of the sport glasses shown in FIG. 1.

FIG. 6 is a bottom plan view of the sport glasses shown in FIG. 1

DETAILED DESCRIPTION OF THE INVENTION

Figure 1:
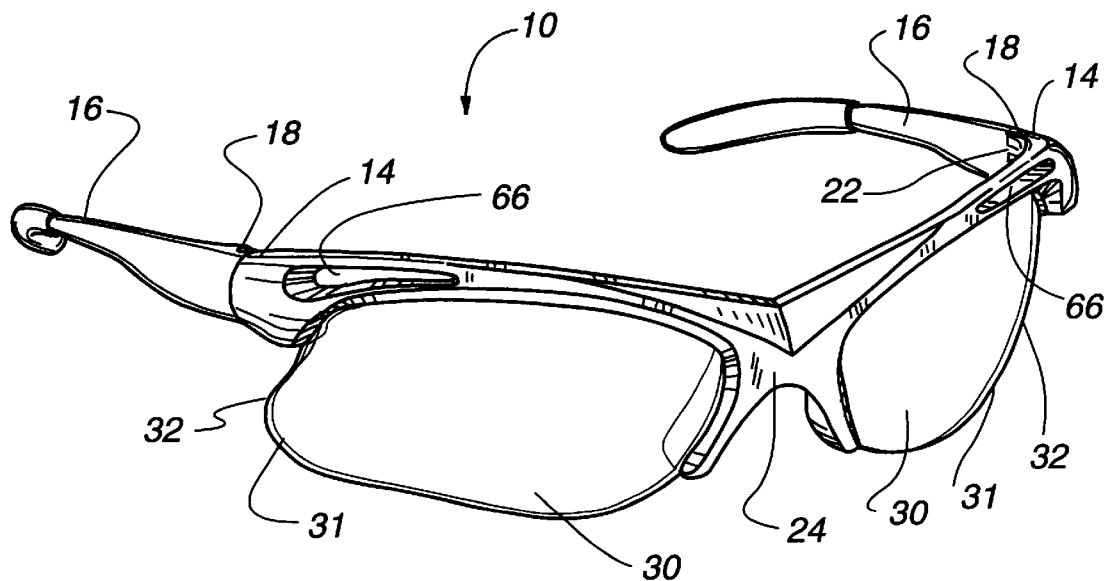
FIG. 1 is a front perspective view of the sport glasses of the present invention.
Figure 2:
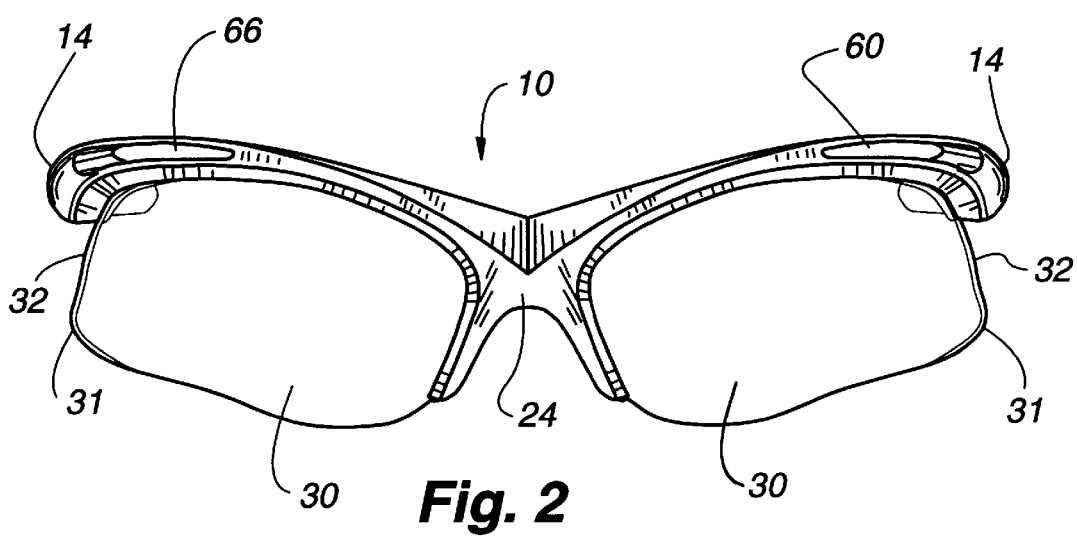
FIG. 2 a is front elevation view of the sport glasses shown in FIG. 1.
Figure 3:
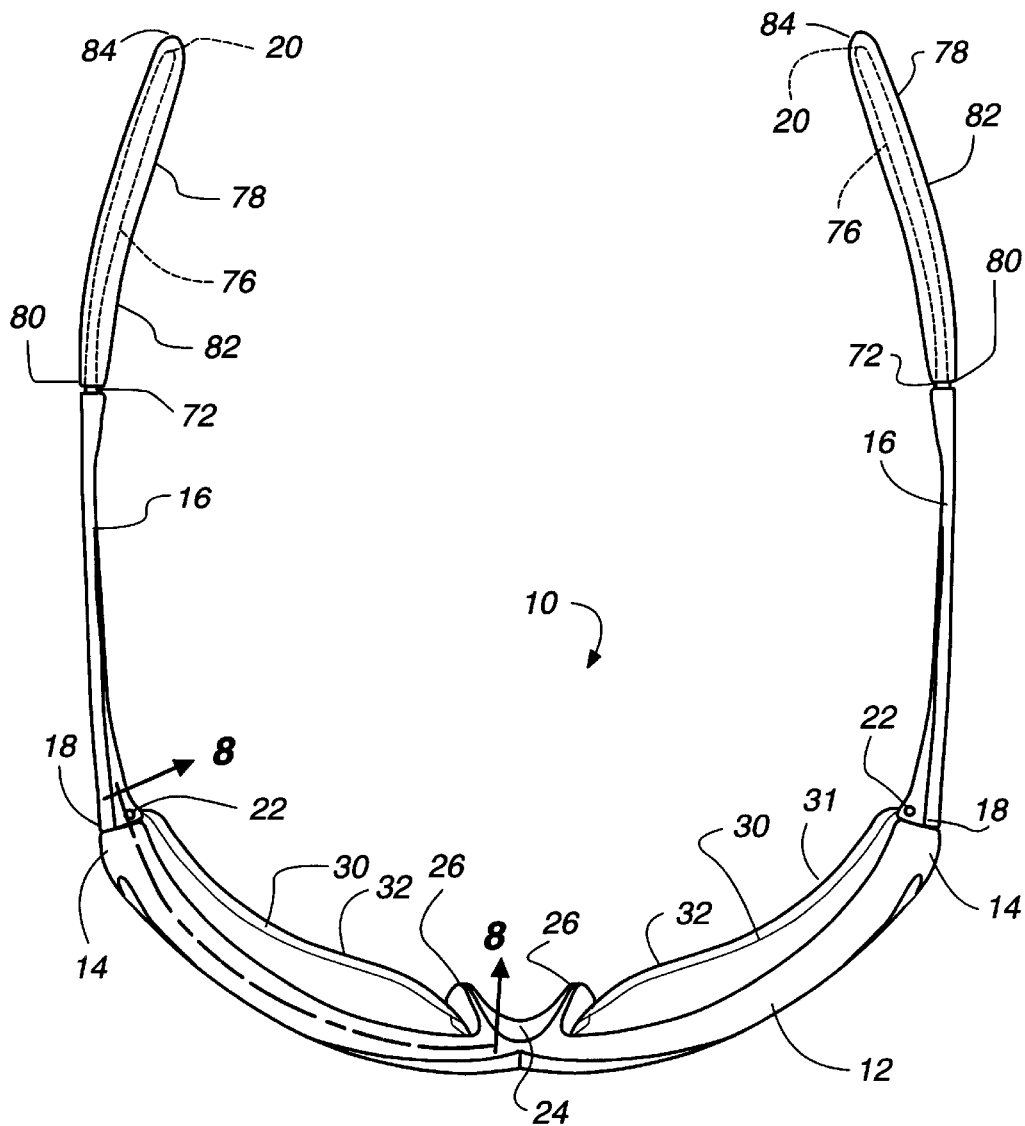
FIG. 3 is a top plan view of the sport glasses shown in FIG. 1.

In accordance with the present application, sport glasses 10 of the present invention are shown in FIGS. 1–9. Glasses 10 include a bridge or frame 12 terminating at opposed frame ends 14, and a pair of elongated ear pieces or temples 16, each having a frame mounting end 18 and an opposed temple end 20. A pair of hinges 22 hingedly attach each of frame ends 14 to one of the frame mounting ends 18 of one of the pair of temples 16. A nose piece 24 centrally depends and is integrally formed from frame 12. Laterally extending from nose piece 24 are nose pads 26. A pair of lenses 30 are removeably secured in frame 14, in a configuration further described below.

Figure 7:
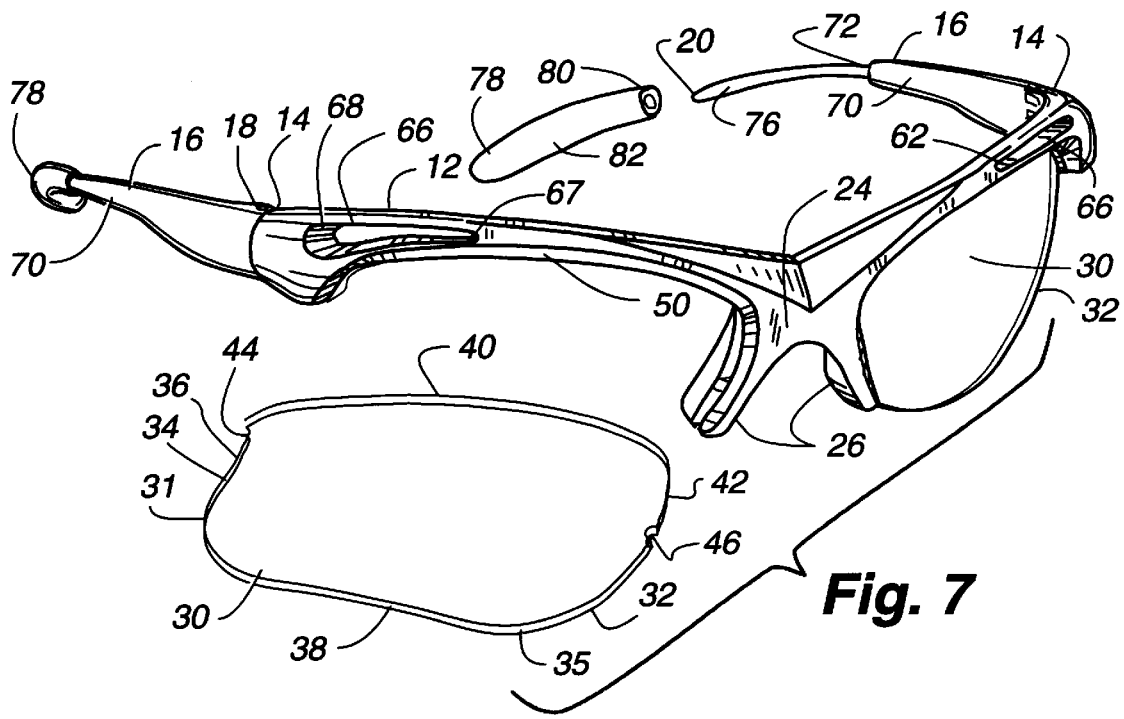
FIG. 7 is an exploded view of the components of the sport glasses shown in FIG 1.
Figure 8:
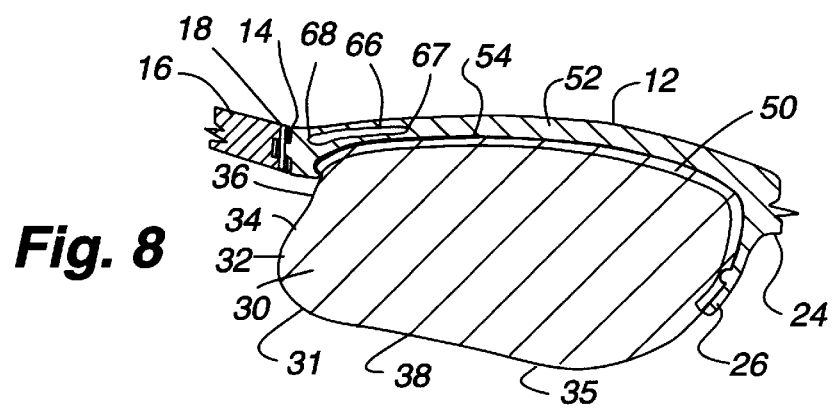
FIG. 8 is a partial section view of one of the lens of the sport glasses shown in FIG. 1, fully mounted in the sport glasses frame, taken substantially in the plane 8—8 of FIG. 3.
Figure 9:
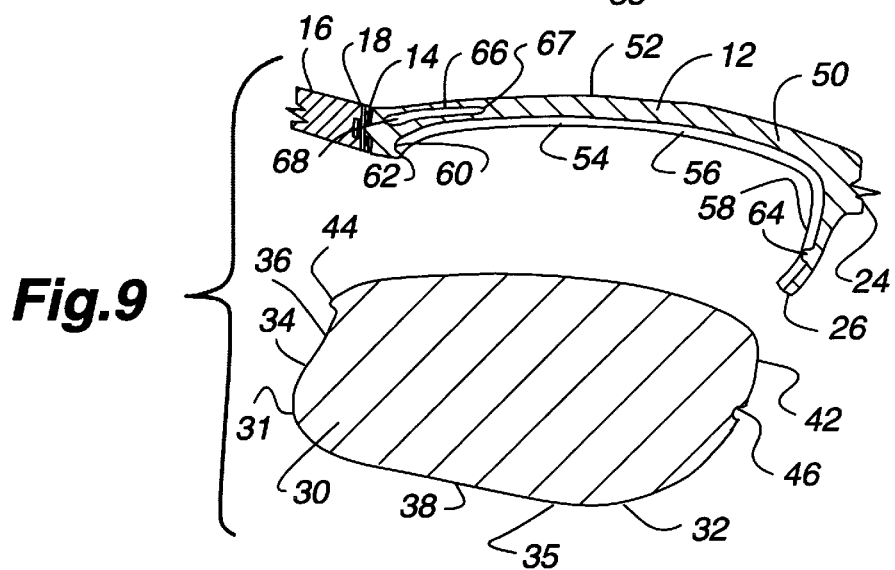
FIG. 9 is an exploded view of the partial section view shown in FIG. 8, with the lens detached from the frame.

Referring now to FIGS. 7–9, it can be seen that each lens 30 is generally convex (when viewed from the front of the glasses, i.e., facing a wearer wearing sport glasses 10), and includes a circumferential edge 31 having an exposed edge 32. Exposed edge 32 includes a side edge 34 and a lower edge 35. Side edge 34 includes a concave side edge portion 36. Lower edge 35 includes a concave lower edge portion 38. Circumferential edge 31 also includes an upper edge 40 and an interior edge 42. Upper edge 40 intersects side edge 34 at an outer lens prong 44 formed in circumferential edge 31. Formed in interior edge 42 is an inner lens notch 46.

Formed in frame 12 is a lower frame edge 50 which is bisected by centrally depending nose piece 24 to form a pair of lower frame portions 52. Each of the pair of lower frame portions 52 is a mirror image of the other of the lower frame portions 52, it being understood that the description of one of the lower frame portion 52 which follows applies to both lower frame portions 52. Formed in lower frame portion 52 is a channel 54 which extends generally laterally adjacent frame end 14 in a sweeping arc, defining a substantially lateral channel portion 56 until it contacts centrally depending nose piece 24, at which point channel 54 curves generally perpendicularly downward to form a substantially vertical channel portion 58. An outer frame notch 60 is formed at an outer end 62 of lateral channel portion 56. An inner frame prong 64 is formed midway along vertical channel portion 58.

Each of the pairs of channel 54 is sized to releasably retain a portion of circumferential edge 31 of one of the lenses 30, with upper edge 40 of lens 30 positioned in lateral channel portion 56 and interior edge 42 of lens 30 positioned in vertical channel portion 58. Each lens 30 is releasably retained by snap-fit engagement of a first detent comprising outer lens prong 44 and outer frame notch 60, and snap-fit engagement of a second detent comprising inner frame prong 64 and inner lens notch 46. It should be understood that while the detent configuration just described is preferred, the prong and notch of each detent may be interchanged.

Frame 12 further includes a pair of tapered ventilating slots 66, one each formed adjacent one of frame ends 14. To maximize the size of ventilating slots 66 without compromising the structural integrity and strength of fame 12, ventilating slots 66 are narrower at inward ends 67 thereof and wider and outward ends 68 thereof, giving each of ventilating slots 66 a somewhat triangular shape.

Figure 4:
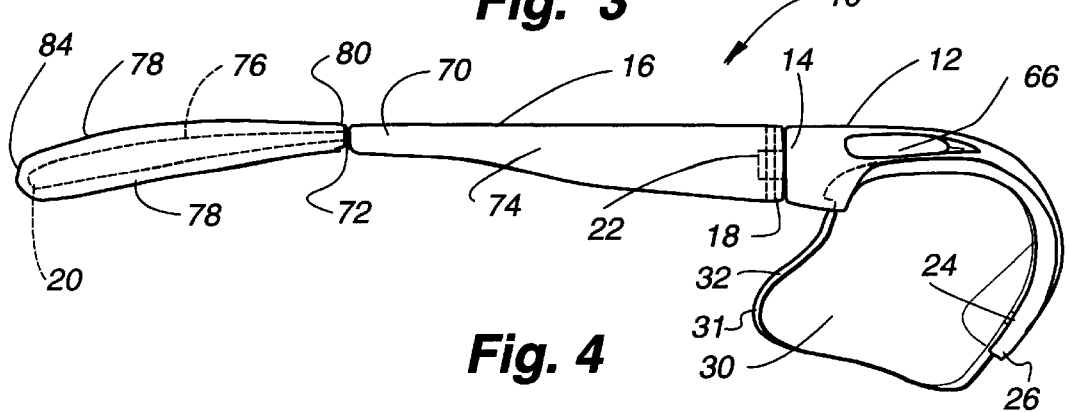
FIG. 4 is a side elevation view of the sport glasses shown in FIG. 1, the opposite side being a mirror image thereof.

Referring now especially to FIGS. 4 and 7, it can been seen that each temple 16 has a height which is greatest adjacent frame mounting end 18. The height of temple 16 then gradually decreases to form a narrowed mid portion 70 of temple 16. Mid portion 70 necks down to form a neck 72 at a position intermediate frame mounting end 18 and opposed temple end 20, defining thereby forward temple portion 74 which extends from frame mounting end 18 to neck 72. Rearward temple portion 76 is a rod-shaped arcuate portion of temple 16 which extends from neck 72 to temple end 20. Covering each rearward temple portion 76 is a hollow neoprene gripping member 78 which is flush at its forward end 80. Mid portion 70 of temple 16 widens to form intermediate portion 82 and narrows at rounded tip 84.

The sport glasses of the present invention are generally conforming to the upper facial structure of the wearer, thereby providing the aerodynamic sleekness and maximized peripheral vision preferred by wearers involved in outdoor activities. Despite the closely confirming shape of the sport glass lenses of the present invention, fogging is decreased by limiting the extension of the lenses around the side of the head of the wearer and by the presence of the ventilating slots on the ends of the frame adjacent the hinges. Ventilation provided by the ventilating slots also serves to cool the wearer. In particular, the broader outward ends 68 of ventilating slots 66 give greater air flow near the temples of the wearer, which allows circulation of air across the forehead and down the sides of the face of the wearer.

The form fitting gripping member pairs mounted to the end of the temples are shaped so as to keep the sport glasses of the present invention intact during athletic activity, without the uncomfortable bulkiness associated with after market tubular gripping members mounted to separately purchased sun glasses. In particular, the slim leading edge of the gripping members, which are flush at the point of intersection with the mid portion of the temple, and the narrowed trailing end together minimize irritation to the back of the ear and side of the head.

The removable configuration of lens pairs of the present invention allows for ready substitution of lens of different tinting or prescription. Indeed, a lens pair of the present invention may have different prescriptions, thus allowing for differential correction of the vision both eyes.

Presently preferred embodiments of the present invention and many of its improvements have been described with a degree of particularity. It should be understood that this description has been made by way of preferred examples, and that the invention is defined by the scope of the following claims.

What is claimed is:

1. Sport glasses for a wearer comprising:
    a frame comprising:
        a substantially laterally extending arcuate upper portion having opposing frame ends,
        a nose piece centrally depending from said arcuate upper portion of said frame and having pair of nose pads extending therefrom,
        a pair of temples, each having a frame mounting end and an opposed temple end, and
        a pair of hinges, each attaching one of said temples at said frame mounting end to said opposed frame end; and
    a pair of convex lenses, each said lens defining an exposed edge having a side edge and a lower edge, each said side edge having a concave side edge portion, and each said lower edge having a concave lower edge portion,
    wherein when said wearer is wearing said sport glasses, said exposed edges of said lenses substantially conform to but are spaced apart from said the adjacent facial structure of the wearer.

2. Sport glasses in accordance with claim 1, wherein said temple pairs each further include a forward temple portion adjacent said frame mounting end and extending to a point intermediate said frame mounting end and said opposed temple end, and a rearward temple portion extending from said intermediate point to said opposed temple end, and wherein said sport glasses further comprise:
    a pair of gripping members, one each covering said rearward temple portion of one of said temples, terminating in a tip at said opposed temple end, and substantially flush with said forward temple portion of said temple at said intermediate point.

3. Sport glasses in accordance with claim 1, wherein each of said lenses is removable and replaceable by the wearer.

4. Sport glasses in accordance with claim 3, wherein said arcuate upper portion of said frame includes a lower frame edge in which a receiving channel is formed, each of said lenses has an upper lens edge and an inner lens edge adapted to be received in said receiving channel, and at least one detent is formed by releaseable engagement of a portion of one or both of said upper and inner lens edges with said lower frame edge.

5. Sport glasses in accordance with claim 3, wherein said temple pairs each further include a forward temple portion adjacent said frame mounting end and extending to a point intermediate said frame mounting end and said opposed temple end, and a rearward temple portion extending from said intermediate point to said opposed temple end, and wherein said sport glasses further comprise:

a pair of gripping members, one each covering said rearward temple portion of one of said temples, terminating in a tip at said opposed temple end and substantially flush with said forward temple portion of said temple at said intermediate point.

6. Sport glasses in accordance with claim 4, wherein said temple pairs each further include a forward temple portion adjacent said frame mounting end and extending to a point intermediate said frame mounting end and said opposed temple end, and a rearward temple portion extending from said intermediate point to said opposed temple end, and wherein said sport glasses further comprise:

a pair of gripping members, one each covering said rearward temple portion of one of said temples, terminating in a tip at said opposed temple end and substantially flush with said forward temple portion of said temple at said intermediate point.

7. Sports glasses in accordance with claim 1, wherein a pair of forwardly and rearwardly facing slots are formed in said arcuate upper portion of said frame, each slot adjacent one of said opposed frame ends, for providing ventilation and minimizing fogging of the lenses when the sports glasses are worn by the wearer.

8. Sports glasses in accordance with claim 2, wherein a pair of forwardly and rearwardly facing slots are formed in said arcuate upper portion of said frame, each slot adjacent one of said opposed frame ends, for providing ventilation and minimizing fogging of the lenses when the sports glasses are worn by the wearer.

9. Sports glasses in accordance with claim 3, wherein a pair of forwardly and rearwardly facing slots are formed in said arcuate upper portion of said frame, each slot adjacent one of said opposed frame ends, for providing ventilation and minimizing fogging of the lenses of the sports glasses when worn by the wearer.

10. Sports glasses in accordance with claim 4, wherein a pair of forwardly and rearwardly facing slots are formed in said arcuate upper portion of said frame, each slot adjacent one of said opposed frame ends, for providing ventilation and minimizing fogging of the lenses when the sports glasses are worn by the wearer.

11. Sports glasses in accordance with claim 5, wherein a pair of forwardly and rearwardly facing slots are formed in said arcuate upper portion of said frame, each slot adjacent one of said opposed frame ends, for providing ventilation and minimizing fogging of the lenses when the sports glasses are worn by the wearer.

* * * * *